(12) United States Patent (10) Patent No.: US 9,319,110 B2
Kopychev et al. (45) Date of Patent: Apr. 19, 2016

(54) USER INTERFACE POWERED VIA AN INDUCTIVE COUPLING

(71) Applicants: Baxter International Inc., Deerfield, IL (US); Baxter Healthcare S.A., Glattpark (CH)

(72) Inventors: Andrey Kopychev, Clearwater, FL (US); Gideon Hecht, Seminole, FL (US); Peter J. Wellings, Palm Harbor, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 175 days.

(21) Appl. No.: 14/073,552

(22) Filed: Nov. 6, 2013

(65) Prior Publication Data

US 2014/0062996 A1   Mar. 6, 2014

Related U.S. Application Data

(63) Continuation of application No. 12/429,709, filed on Apr. 24, 2009, now Pat. No. 8,587,516.

(51) Int. Cl.
*G09G 3/00* (2006.01)
*H04B 5/00* (2006.01)
*A61M 1/14* (2006.01)
*G06F 1/16* (2006.01)
*H02J 7/02* (2006.01)

(52) U.S. Cl.
CPC ............... *H04B 5/0075* (2013.01); *A61M 1/14* (2013.01); *G06F 1/1615* (2013.01); *G06F 1/1681* (2013.01); *G06F 1/1683* (2013.01); *G09G 3/00* (2013.01); *H02J 7/025* (2013.01); *A61M 2205/3561* (2013.01); *A61M 2205/3584* (2013.01); *A61M 2205/3592* (2013.01); *A61M 2205/502* (2013.01)

(58) Field of Classification Search
None
See application file for complete search history.

(56) References Cited

U.S. PATENT DOCUMENTS

| 5,325,046 | A  | 6/1994  | Young et al.   |
| 6,143,181 | A  | 11/2000 | Falkvall et al.|
| 6,256,129 | B1 | 7/2001  | Kim et al.     |
| 6,803,744 | B1 | 10/2004 | Sabo           |

(Continued)

FOREIGN PATENT DOCUMENTS

| EP | 1148406 A2 | 10/2001 |
| EP | 1355221    | 10/2003 |

OTHER PUBLICATIONS

International Preliminary Report on Patentability for International Application No. PCT/US2010/031365 mailed on Jul. 11, 2011.

(Continued)

*Primary Examiner* — Joseph Haley
*Assistant Examiner* — Emily Frank
(74) *Attorney, Agent, or Firm* — K&L Gates LLP (57) ABSTRACT

A hinge is provided for mechanically and electrically coupling a machine and a display wirelessly. The hinge includes a machine portion having a first transceiver for wirelessly sending a signal concerning an operation or status of the machine and a display portion having a second transceiver for wirelessly receiving the operating signal. The hinge machine portion and the hinge display portion are mechanically connected so as to: (i) swivel with respect to each other; or (ii) tilt with respect to each other.

19 Claims, 9 Drawing Sheets

(56) References Cited

U.S. PATENT DOCUMENTS

| | | | |
|---|---|---|---|
| 6,906,495 | B2 | 6/2005 | Cheng et al. |
| 7,027,311 | B2 | 4/2006 | Vanderelli et al. |
| 7,239,110 | B2 | 7/2007 | Cheng et al. |
| 7,312,607 | B2 | 12/2007 | Nygaard |
| 2004/0042482 | A1* | 3/2004 | Smith et al. ............. 370/463 |
| 2006/0082518 | A1* | 4/2006 | Ram ......................... 345/1.1 |
| 2006/0199620 | A1 | 9/2006 | Greene et al. |
| 2007/0112603 | A1 | 5/2007 | Kauthen et al. |
| 2007/0298846 | A1 | 12/2007 | Greene et al. |
| 2008/0000477 | A1* | 1/2008 | Huster et al. ......... 128/204.23 |
| 2008/0029707 | A1* | 2/2008 | Kari ................... A61B 6/4405 250/370.09 |
| 2008/0136622 | A1 | 6/2008 | Seo et al. |
| 2008/0169910 | A1 | 7/2008 | Greene et al. |
| 2008/0200869 | A1 | 8/2008 | Bedingfield |
| 2008/0311962 | A1* | 12/2008 | Demuynck ........... G06F 1/1616 455/575.1 |
| 2009/0008306 | A1 | 1/2009 | Cicchello et al. |
| 2011/0110670 | A1* | 5/2011 | Atkinson .................. 398/135 |
| 2012/0153732 | A1* | 6/2012 | Kurs et al. ................. 307/104 |

OTHER PUBLICATIONS

International Search Report and Written Opinion for International Application No. PCT/US2010/031365 mailed on Jan. 14, 2011.
European Office Action—European Appl. No. 10 717 346.0-1662—mailed Nov. 17, 2014 (6 pages).
European Office Action—European Appl. No. 10 717 346.0-1662—mailed Jun. 12, 2015 (6 pages).

* cited by examiner

USER INTERFACE POWERED VIA AN INDUCTIVE COUPLING

PRIORITY

This application claims priority to and the benefit as a continuation application of U.S. patent application Ser. No. 12/429,709, filed Apr. 24, 2009, entitled, "User Interface Powered Via an Inductive Coupling", the entire contents of which is incorporated herein by reference and relied upon.

BACKGROUND

The present disclosure relates to user interfaces or display devices for operating machines, and in particular to interfaces that communicate wirelessly with an operating portion of the machine, such as a medical machine or other machine.

User interfaces, such as video monitors, are used throughout industry. In the medical industry, such devices are used in a stand-alone manner, e.g., they are connected via a cable to a medical machine or instrument, or they are closely connected to a machine, e.g., to a dialysis machine. User interfaces in the medical industry are subject to certain requirements not found in other industries. The devices typically operate in a clean or germ-reduced environment. The display devices in many cases need to be viewed by multiple persons and from different angles.

There is at least one drawback, however, to the use of computers and monitors by multiple persons. Germs and other causes of infection, such as bacteria, viruses or other harmful organisms, may be placed on the surface of the computer and especially on user interfaces. A subsequent user, such as a caregiver, may accidentally become contaminated with such an organism when adjusting the display or monitor. The organism may then be passed to one or more patients, causing infections to the detriment of those patients. In addition to the caregiver, the patient may also use and handle the monitor. In some hospitals, patients during their recuperation periods have access to a computer and a monitor. Patients may compose and answer e-mails, do a variety of work, perform Internet searches, or play computer games using a bedside computer with a monitor or computer interface requiring adjusting or repositioning.

One solution to the problem of passing infection between users is to limit the use of the interface to a single user, but this solution would be expensive. Of course, the interface may be cleaned between uses or between users, but this solution poses an additional problem in the time involved in waiting and cleaning. In addition, the interface and its connections should be water-proof to withstand multiple cleaning operations. In addition, it would be very helpful if the device were powered by the machine or at least did not require its own power cord or power supply, which simply adds to the clutter when the machine and user interface are set up and operated.

A need therefore exists for a moveable user interface or display device which is moveably flexible and which can be cleaned readily and powered remotely.

SUMMARY

The present disclosure provides a user interface, such as a display device or computer monitor, which is powered via a wireless, inductive coupling, allowing the interface to be completely removed from a base or a machine without having to manipulate a cord or wire harness. Configuring the interface to be removed in this way allows it to be turned readily in multiple orientations for operating or cleaning. This wireless configuration also allows the user interface to be rotated without being encumbered by a power cord. The user interface in one embodiment rotates about two axes, a vertical axis and a horizontal axis. The user interface can, for example, rotate a full three-hundred sixty degrees about a vertical axis of a base or a medical machine, enabling a doctor, nurse or patient to turn the user interface for viewing regardless of which side of the machine the person is facing.

The user interface in one embodiment has sealed seams and requires no opening for power, resulting in a device that is virtually hermetically sealed. This configuration prevents liquids from leaking into and damaging the device. In one embodiment, the system is a three-piece system including a base or machine, a hinge housing connected rotatably to the base and the user interface connected rotatably to the hinge housing. The base inductively or wirelessly powers the hinge housing, which in turn inductively or wirelessly powers the user interface. Here, a first secondary coil is located within a separate hinge housing. The hinge housing in turn includes a second, primary coil, which inductively powers a second, secondary coil located within the user interface. The hinge housing, like the user interface, has sealed seams and requires no opening for power, thus preventing liquids from leaking into the housing.

In one embodiment, both power level and signal level currents are transmitted inductively from the base to the hinge housing, and from the hinge housing to the user interface (or directly from the base to the hinge housing). In another embodiment, only power level currents are transferred inductively. The transferred power in turn powers a transceiver, such as a radio frequency transmitter/receiver that sends and receives signals wirelessly between the base or underlying machine and the user interface.

As discussed herein, in one embodiment, the user interface operates with a medical machine, such as a dialysis machine. The dialysis machine includes a housing or enclosure, with internal components such as for example, pumps, pump actuators, heaters, valves, valve actuators, and sensors. The machine includes a plug or other contact configured to receive branch or line power, e.g., 120 VAC electricity, from a convenience outlet in a hospital, treatment center, home or other location in which treatment can take place. The electricity powers the equipment and in one embodiment also powers a controller with a transceiver for communicating with the user interface as discussed above. The line power also powers a primary inductor coil either directly or via a power regulator that regulates the line power to a desired voltage and frequency. The user interface houses a secondary coil. The secondary coil is coupled inductively to the primary coil and is configured to supply power to electrical components of the user interface, such as control circuitry, a video controller, touch screen controller, and video monitor. The secondary coil can also power a transceiver located within the user interface in one embodiment, the transceiver communicating with the dialysis machine base.

The user interface is connected moveably or hingedly to the housing. For example, the user interface can be hinged along a plurality of axes (tilt and swivel) relative to the housing. The machine housing in one embodiment includes a hinge portion coupled to a hinge portion of the user interface, wherein the wireless coupling is located at the hinge portions.

In an alternate two-piece embodiment, the equipment and primary coil are located inside the housing and the secondary coil is located within the user interface. For example, the primary coil can be located within a hinged portion of the machine housing and the secondary coil can be located within a mating hinged portion of the user interface or monitor. In another embodiment, the secondary coil is located within a separate hinge housing, sending power to the hinged monitor via electrical contacts.

The user interface can include any one or more of: (i) a video monitor, (ii) a touch screen overlay; and (iii) at least one electromechanical input device. The dialysis machine main housing includes controllers and electronics configured to operate the dialysis equipment, such as a pump, a heater and valve actuator controllers and electronics. The machine housing controllers receive wireless signals from the user interface controllers telling the machine controllers how to operate the equipment. The machine controllers also send information wirelessly to the user interface controllers providing information on the operation and status of the dialysis equipment.

The primary coil of the base or instrument housing is in one embodiment surrounded by an electromagnetic energy shield, such as an aluminum container or box. The primary coil can extend substantially circumferentially about the secondary coil, or vice-versa. While the coupling is inductive in one embodiment, the coupling can alternatively be capacitive or via radio frequency. As discussed, the wireless coupling can be configured to perform signal level communication between the machine housing and the user interface. For example, there can be different wireless couplings, with a first wireless coupling for supplying electric power and a second wireless coupling for signal level communication.

The power transfer is configured in one embodiment such that the machine housing supplies power to the user interface electronics when the user interface is coupled mechanically to the housing but stops the transmission of power when the user interface is removed from the housing. The user interface can include a power storage device, e.g., battery or capacitor, which stores power such that the user interface remains operable when removed from the housing.

One embodiment includes an operating machine with a moveable display. The operating machine includes a housing for the operating machine, an operating section within the housing, a primary induction coil carried by the housing, a user interface connected hingedly to the housing without wires, and a secondary induction coil carried by the user interface, the secondary induction coil coupled inductively to the primary induction coil and configured to wirelessly supply power to the user interface while the machine is operating, to wirelessly supply at least one signal to and from the user interface while the machine is operating, or to wirelessly supply power to the user interface and to wirelessly supply at least one signal to and from the user interface while the machine is operating. An operating machine is a machine which performs an operation, such as a medical machine that performs a diagnostic operation or a therapeutic function. Examples are an ultrasound machine, a CT scanner and a dialysis machine.

Another embodiment includes an operating machine with a moveable display. The operating machine includes a housing for an operating medical machine, a display movably connected to the dialysis housing without wires, at least one sensor within the dialysis housing for sensing a condition of the operating medical machine and sending a signal concerning an operation or a status of the machine. The operating machine also includes a first signal processing circuitry connected to the sensor for processing the signal, a first transceiver within the housing for wirelessly sending the signal, a second transceiver within the display for wirelessly receiving the signal, and second signal processing circuitry for displaying on the display an indication of the operation or the status of the medical operating machine from the signal.

Another embodiment includes an operating machine with a moveable display. The operating machine includes a housing for an operating dialysis machine, at least one pump within the housing for pumping dialysis fluid, a user interface coupled wirelessly and removeably to the housing, and also includes electronics associated with the housing and the user interface and configured for the housing electronics to supply power to the user interface electronics when the user interface is near the housing and for the housing electronics to automatically cease supplying power to the user interface when the user interface is removed from the housing.

Another embodiment is a method of providing a dialysis therapy. The method includes steps of providing a dialysis machine having a user interface removeably and wirelessly connected to the dialysis machine. The method also includes a step of generating signals indicative of an operation or status of the dialysis machine, an optional step of providing a dialysis therapy, and a step of wirelessly sending to the user interface at least one operating signal from the dialysis machine.

It is accordingly an advantage of the present disclosure to provide a medical instrument having a wirelessly coupled user interface.

It is another advantage of the present disclosure to provide a medical user interface removable for cleaning.

It is a further advantage of the present disclosure to provide a medical instrument having a user interface that can be rotated in multiple directions.

It is yet another advantage of the present disclosure to provide a medical instrument having a user interface that can be rotated in multiple directions.

It is a further advantage of the present disclosure to provide a user interface, machine housing and interface between same, which is resistant to spills of medical fluid.

It is a further advantage of the present disclosure to provide a dialysis machine with a remotely-powered, that is wirelessly powered, user interface.

Additional features and advantages are described herein, and will be apparent from, the following Detailed Description and the figures.

DETAILED DESCRIPTION

Figure 1:
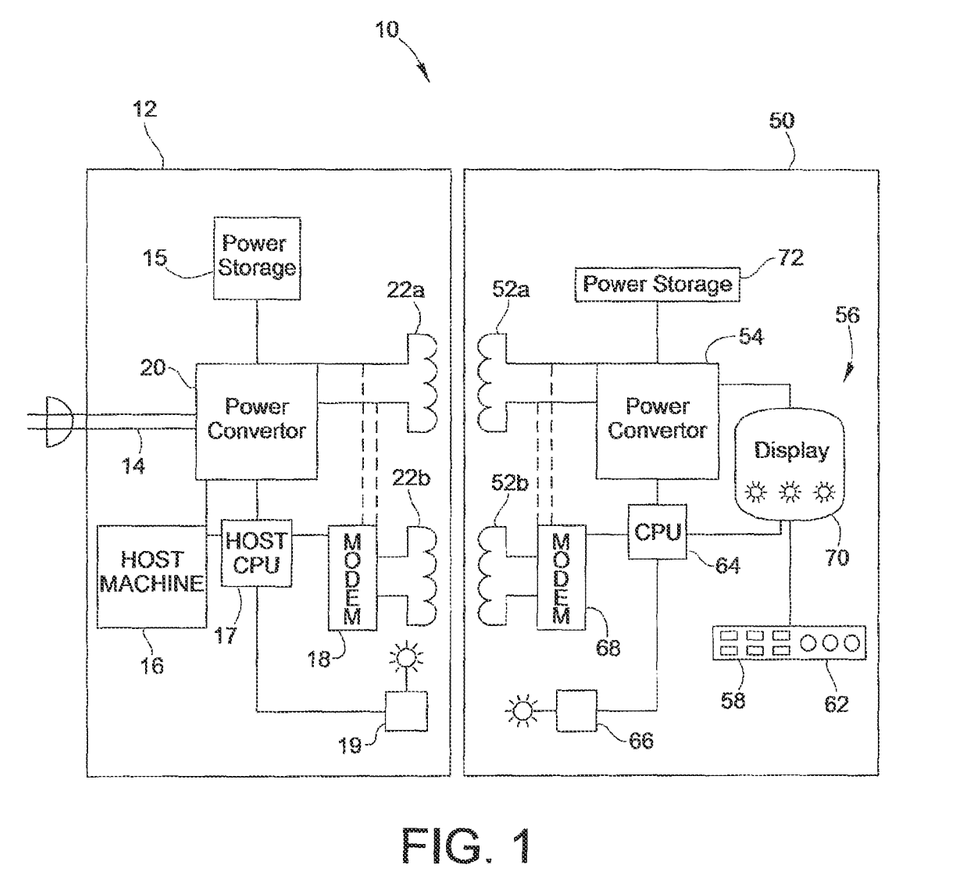
FIG. 1 is a schematic view of a first embodiment of a two-piece operating machine.

Referring now to the drawings and in particular to FIG. 1, system 10 illustrates one embodiment of an electrical schematic for the wirelessly coupled medical device display of the present disclosure. For the sake of illustration, system 10 is shown in a two-piece configuration, e.g., a base that includes a housing, and a hinged display. As shown herein, however, the teachings of FIG. 1 are equally applicable to a three-piece configuration (e.g., base with housing, separate hinge housing and display). System 10 includes a base and housing 12 and a user interface or display 50. Base 12 in the illustrated embodiment is a machine, such as a medical machine or a dialysis machine. Other machines with separate interfaces or video screens may also be used. Alternatively, the machine is another type of medical delivery machine, such as one for delivering a drug or other medical fluid intravenously to the patient. The machine includes a branch or line power source contact 14, such as a plug for use in a convenience outlet. The plug is illustrated for 110-120 VAC service but is configured alternatively for whichever line voltage is available, e.g., 220-240 VAC. Line power is converted and regulated as desired by power conversion circuitry within power converter 20. Machine 12 may also include a power storage device 15, such as a battery.

The branch or line source powers a plurality of electrical components within medical instrument 12, including machine components 16, a host machine computer 17, modulator/demodulator (modem) 18 and a radio transceiver 19 (optional). Machine components can include any suitable machine components associated with the particular machine, such as an apheresis machine, a peritoneal dialysis machine, hemodialysis machine, hemofiltration machine, hemodiafiltration machine or continuous renal replacement machine. Dialysis machines can for example include pumps (blood, dialysate, heparin and saline), valve actuators, heater elements, sensors, controllers, etc., which receive line or branch power.

In the illustrated embodiment, the line or branch source powers a radio transceiver 19. Transceiver 19 is for example a two-way, radio frequency transmitter and receiver, which communicates wirelessly with a like transceiver 66 located within user interface 50. Transceivers 19, 66 send commands back and forth from instrument 12 and user interface 50. For example, when an operator or patient enters a command into user interface 50, a corresponding signal is sent from transceiver 66 to transceiver 19, which relays the signal to the appropriate controller within the host computer 17 and machine components 16, which in turn controls the appropriate equipment. Radios 19, 66 may be used in one wireless method of controlling machine 12 from display 50. If the radios are used in place of the data transformer, any appropriate non-interfering radio frequency may be used. Appropriate equipment may be that suitable for Bluetooth™, a short range, low-power radio protocol governed by several versions of IEEE Standard 802.15.1. For example, a Class 3 system, with a maximum transmitted power of 1 mW, is sufficient for data transfer over about 1 meter, which is sufficient for the contemplated application. Other classes may be used. Equipment is available from several manufacturers.

The inductors, and other devices for wireless transmission, are described herein as primary and secondary inductors, or other devices, for generating signals and sending signals in the dialysis machine and receiving signals in the user interface, i.e., they act as electrical transformers. It is understood that their functions may be reversed by the appropriate circuitry, so that commands entered into the user interface will generate signals in the user interface for transmitting wirelessly to the dialysis machine, the signals received by the dialysis machine in a mirrored process. Thus, in an alternative embodiment, the signals between the host computer 17 and the display controller 64 are generated and sent back and forth from instrument 12 and user interface 50 via the wireless or inductive coupling discussed in connection with coils 22a, 22b and 52a, 52b. The wires for primary and secondary signal coils 22a, 52a are shielded in this embodiment and use primary and secondary coils that are separated from primary and secondary power coils 22b, 52b.

In a first alternative embodiment, power is transferred from machine 12 to user interface 50 via a power transformer formed by primary coils 22a, 52a while data is transferred via a data or signal transformer formed by primary coils 22b, 52b. Both power and data are transferred in the form of pulses. In one embodiment, power is transferred using a frequency from about 20 kHz to 1 MHz while data is pulsed at about ten times the rate of power pulsing, e.g., about 200 kHz to 10 MHz. Signals on the machine 12 side are sent from the host computer 17 to modem 18 for the appropriate modulation and processing. The modulated signals are then sent to the data transformer formed by inductor coils 22b, 52b for transfer. The signals received by modem 68 on the interface or display 50 side are then modulated as necessary and sent to the display computer 64 for appropriate processing. When signals are sent from the interface side to the machine side, the reverse process takes place. If the frequency of the power and data signals are widely separated, as mentioned above, a single transformer pair, such as that formed by induction coils 22a, 52a may be used to send both power and data at once. The signals are generated and separated by the modems 18, 68 with sufficient clarity. Thus, a third embodiment is the use of a single transformer to wirelessly power the user interface and to wirelessly send signals between the machine and the user interface.

The line or branch power source 14 also powers a power regulator or conditioner 20. Regulation circuitry 20 includes any electronics needed to generate the appropriate power and signals for the machine 12 and primary induction coils 22a, 22b. The electronics can include zero-crossing switching electronics, which operate a transistor, such as an insulated gate bi-polar transistor ("IGBT") type switching device, or a metal oxide field effect transistor ("MOSFET"). The switching device in one embodiment is a MOSFET 5-10 amp transistor which has zero voltage across an associated transistor or zero current through the transistor when transitioning between power ON/OFF. This capability helps to reduce power losses in the switching element as the element transitions from its ON to OFF state or its OFF to ON state. The switching device in turn controls a quasi-resonant LC circuit in one embodiment, which energizes primary coil 22. Primary coil 22b in the illustrated embodiment and in each of the embodiments illustrated herein can range from about 0.5 to about 50 µH in inductance. Power coil 22b can be energized to deliver sufficient power, depending on power losses in primary power coil 22b. The LC circuit can have a resonant frequency of about 20 to about 200 kHz, although other frequencies may be used, up to 1 MHz. The maximum power delivery required is typically about 30 W to 100 W, although power requirements in other embodiments may vary from 2 W to 150 W. A bridge rectifier can also be connected between power source 14 and the quasi-resonant LC circuit.

Suitable materials for primary coils 22a, 22b and secondary coils 52a, 52b of the machine 10 and user interface 50 include 20-30 ga magnet wire, although any convenient materials and conductors may be used, including heavier and finer gauge wire or litz wire. Signal coils 22a and 52a are shielded from the environment via an electromagnetic shield 24. Electromagnetic shield 24 is in one embodiment an aluminum box that surrounds all sides of coils 22a and 52a. Because coils 22a, 22b and 52a, 52b are located inside different apparatuses, the unshielded surfaces of instrument 12 and user interface 50 are exposed when pulled apart. Power to coils 52a, 52b is cut when the devices 12 and 50 are pulled open, in one embodiment.

In the illustrated embodiment, primary coils 22a, 22b induce an electrical current into secondary coils 52a, 52b. The current is circulated through power regulation circuitry 54, which can include any necessary voltage regulation, filtering, and so forth. The secondary coils 52a, 52b in one embodiment are assembled within the primary coils 22a, 22b to minimize the air gap or distances between the coils, thus minimizing power losses and maximizing power transfer from the housing or base 12 to the user interface 50. The lead wires in one embodiment are on the same side of each coil or inductor to facilitate insertion and removal of the secondary coils from the primary coils if disassembly is necessary.

The coils in this embodiment are molded within a suitable dielectric, e.g., a plastic with high electrical resistance, with only two wire leads exiting each coil molding. It will be recognized that the coil-housings may be hinge components, the hinges securing the display device or user interface to the base or housing of the dialysis machine. The hinges allow tilting or swiveling of the display with respect to the housing, and the hinge components are clearly in close proximity to each other. Tilting refers generally to revolution about a horizontal axis while swiveling refers generally to revolution about a vertical axis. Thus, it is logical that the hinges may incorporate induction coils for transferring power from the base or housing to the user interface.

Power induced from primary coils 22a, 22b to secondary coils 52a, 52b and conditioned at circuitry 54 is used to power the electrical components within user interface 50. The electrical components can include video display 70, display computer 64, modem 68, radio 66 and appropriate lights, such as LEDs 56. Video display 70 may be a touch screen with integral switches. User interface 50 need not include a touch screen but may instead be equipped with a user interface 58 that includes switches 62 or other control devices, such as main computer 64 to operate video monitor 70. Further alternatively, a touch screen overlay is placed onto video monitor 70 and is controlled via touch screen controller 60, wherein membrane switches or switches 62 are not used. Further alternatively, both the touch screen and additional switches 62 are provided on user interface 50. User interface 50 can include additional components not shown in FIG. 1 and powered via the wireless coupling of system 10.

It should be appreciated that user interface 50 in one embodiment does not need any external metal or conductive contact to receive power. Thus, user interface 50 can be virtually hermetically sealed to keep medical fluids and body fluids from entering user interface 50. If the display is handled by several people or caregivers in succession, the ease of cleaning can lead to cleaner touch-screen surfaces and fewer chances for spreading of germs or other harmful microorganisms. No power cord links instrument 12 to user interface 50, which can thus be easily removed for cleaning.

In the illustrated embodiment, when secondary coils 52a, 52b are pulled away from primary coils 22a, 22b, user interface 50 ceases to receive power (and signals) from the inductive coupling circuit. Thus in one embodiment, pulling user interface 50 away from instrument 12 acts as a power-off switch, shutting off power to the user interface 50. Alternatively, user interface 50 includes a power storage device 72, such as a lithium battery or other type of storage battery, or a capacitor, which stores power and allows one or more of electrical components 54 to 70 to remain powered after user interface 50 is removed from instrument base 12. Here, a switch 62 or a button controlled by the touch screen overlay turns user interface 50 on and off. This additional switch or button can be provided in addition to the display-removal ON/OFF switch described above. Power storage device 72 is shown receiving power from power regulator circuitry 54, which may include a battery charging circuit. Alternatively, power storage device 72 receives power from secondary coil 52b directly and conditions the power as needed for use with components 56 to 70.

Figure 2:
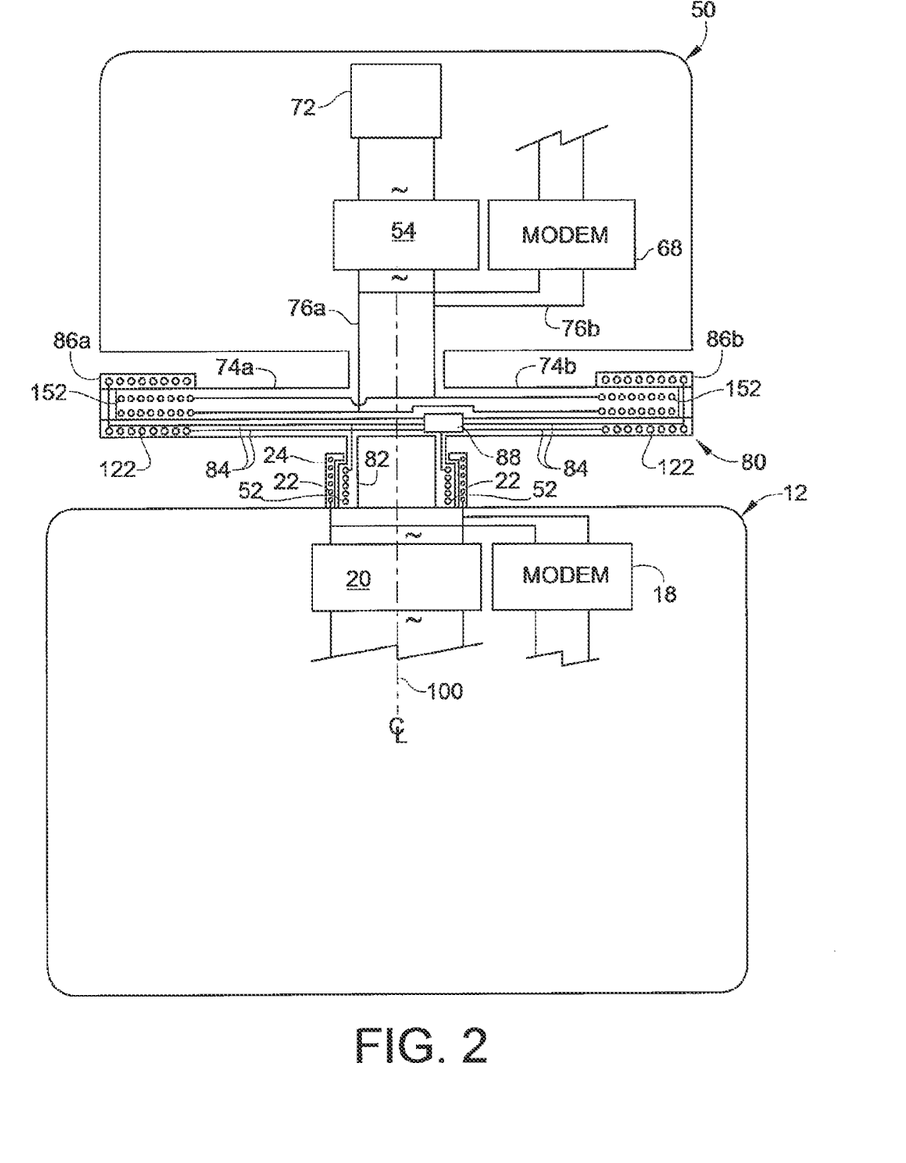
FIG. 2 is an elevation view of a three-piece operating machine.

System 10 of FIG. 1 shows user interface 50 inductively coupled directly to instrument 12. FIG. 2 shows an alternative embodiment in which primary signal coil 22 of instrument 12 is inductively coupled to a secondary signal coil 52 located in a hinge housing 80 and additional circuits in hinges 74a, 74b. In this embodiment, user interface 50 receives power from a storage device within the display, such as a storage battery 72. Signals from instrument 12 are conditioned as necessary by modem 18 and routed simultaneously with power from conditioning circuitry 20 to primary coil 22 within collar 24 and secondary coil 52 within stem 24. Signals induced in the secondary coil 52 are conditioned as necessary by additional conditioning circuitry 88 within hinge housing 80. The conditioned signals are then led by wires 84 to second primary coils 122 within the hinge housing to induce signals in second secondary coils 152 within hinges 74a, 74b. The signals from the secondary coils 152 are then led by wires 76a, 76b to modem 68 and power converter 54 within the monitor housing 50.

Instrument 12 in FIG. 2 includes a base collar 24. Hinge housing 80 includes a vertically disposed stem 82, which rotates within base collar 24 of instrument 12. The hinge housing 80 also includes upper, outer hinge portions 86a, 86b. In an embodiment, collar 24 and stem 82 are locked together, such that hinge housing 80 cannot easily or readily be pulled out of base collar 24, but so that hinge housing 80 can rotate or swivel with respect to collar 24 and instrument 12. The enclosure of instrument 12 including base collar 24 can be metal or plastic. Likewise, hinge housing 80 can be metal or plastic. A housing for user interface 50 is typically plastic, but may be made of a light metal. Base collar 24 may be considered to be a stationary portion of a rotating hinge, with hinge housing 80 an intermediate part that includes a vertically disposed stem that rotates within base collar 24. Outer swivel hinges 86a, 86b, receive inner swivel hinges 74a, 74b of the user interface 50, the inner swivel hinges connected to the user interface in a manner so that they cannot be rotated or swiveled with respect to the user interface.

Primary coil 22 is molded or assembled inside the wall of base collar 24 in one embodiment, such that the coil is not exposed to external touching or contamination. The thickness of collar 24 is sufficient to hold the coil 22 firmly in place without the coil puncturing the wall of base collar 24. However, the walls of collar 24 and stem 82 are kept thin so that the gap between the primary and secondary coils is minimized. This allows for minimal interference with the inductive transfer between primary coil 22 and secondary coil 52. Secondary coil 52 is likewise embedded, e.g., molded into, stem 82 of hinge housing 80, such that secondary coil 52 resides near the outer surface of stem 82. It is desirable to minimize the gap between primary coil 22 and secondary coil 52, consistent with requirements for electrical insulation, structural integrity and ruggedness of the parts.

Stem 82 in one embodiment fits snuggly inside collar 24. Lubricant can be used to aid in the smooth swivel or rotation of user interface 50 within collar 24 of base 12. Current induced into secondary coil 52 travels via wires or traces 84 and conditioning circuitry 88 to second primary coils 122, which are embedded, e.g., molded into, hinge housing 80 at each of hinge ends 86a and 86b. Hinge ends 86a and 86b again embed the coils 122 in such a way so as to hold the coils firmly near the outer surfaces of the hinge ends, but not to provide unnecessary spacing. If the spacing is kept to a minimum, second primary induction coils 122 can in turn inductively impart current into second secondary coils 152 located within hinges 74a, 74b of user interface 50.

Hinges 74a, 74b in one embodiment are made of a hard but flexible plastic or rubber material that can be bent, e.g., 60-70 Shore D durometer, although other elastomers of other hardnesses may be used. In one embodiment, hinge ends 86a and 86b of hinge housing 80 are open at their outside ends, so that the user can move user interface 50 left or right relative to instrument 12, sliding one of hinges 74a, 74b inwardly out of its respective hinge end 86a, 86b. When one of hinges 74a, 74b is free, the user can bend one or both of the hard, flexible hinges, so that the free hinge 74a, 74b rotates upwards and clears its hinge end 86a or 86b, so the user can pull the other hinge out of its respective hinge end to free user interface 50 from base or housing 12.

In one embodiment, hinges 74a, 74b may include outwardly projecting ratcheting notches (not shown), which mate with inwardly projecting notches (not shown) formed on the inside surfaces of hinge ends 86a and 86b of hinge housing 80. In this manner, the user can tilt user interface 50 forward or backward and set the user interface at a desired tilt position with respect to instrument 12. The user can also swivel or rotate user interface 50 about a centerline axis 100 to a desired position. It should be appreciated that the wireless coupling enables user interface 50 to be rotated three hundred sixty degrees about center line axis 100. The user interface is accordingly highly positionable. Power from the transformer is transferred via wires 76a to power converting circuitry 72. Data or signals generated in the second secondary coil 152 travel via wires 76b to modem 68, which conditions the signals for transmission to computer 64 of user interface 50 as described above. The hinges themselves are made from non-conducting engineering plastics, such as nylon.

Figure 3:
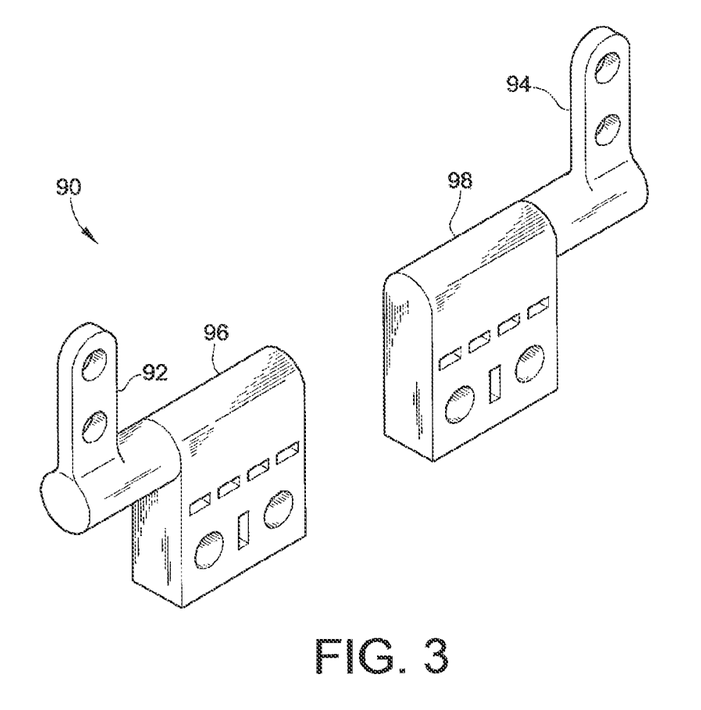
FIG. 3 is a perspective view of one embodiment of a divided hinge.

One embodiment of a hinge is depicted in FIG. 3. This hinge assembly 90 includes left and right portions, with left and right upper or movable portions 92, 94 and left and right lower or stationary portions 96, 98. The hinge portions include mounting apertures as shown, and in this embodiment, the upper portions 92, 94 would be mounted to a viewing screen, such as viewing screen 50 depicted in FIGS. 1-2. Lower portions 96, 98 would mount to a dialysis machine or other instrument, as also depicted in FIGS. 1-2. These hinges include internal springs, such as those marketed by Machine Components Corp., Plainview, N.Y., Southco, Inc., Concordville, Pa., both in the U.S.A. Others, such as those from Reell Precision Mfg. Co., St. Paul, Minn., U.S.A., use internal clips to resist movement. The internal spring or clips provide a constant force to resist movement in either direction, and thus stabilize the tilt position of the screen.

It is understood that such hinges may be used as tilt hinges, so that the position of the screen may be tilted in a manner toward or away from a user, such as a dialysis patient. An example is the hinge 80 in FIG. 1 Such hinges may also be used for a vertical swivel axis, so that the screen may be swiveled for preferential viewing, for instance on one side of a room or another. An example is the hinge that would be used in the stem and collar 24, 82 of FIG. 2. Using dual hinges, e.g., left and right hinges as shown in FIGS. 2-3, facilitates the separation of the power and signal inductive portions.

These "constant force" hinges work by sequential winding and unwinding of the spring or springs within the housings. In the example of FIG. 3, as the screen is tilted backward, away from the user, the internal springs wind up and continue to resist the tilting motion. Because the springs are anchored internally to both the movable and the stationary portions of the hinge housings, the springs resist motion forward and backward and tend to stabilize the screen position, much as the hinges on a laptop computer also stabilize the screen position. The hinge may also incorporate tiny ball detents for additional stabilization of one or more particular angles or orientation of the hinge and thus the screen. For example, the stationary portion may include one or more small hemispherical depressions to match a single detent or protrusion in the moveable portion. When the user swivels (or rotates) the screen to a particular position, the detent moves into the depression, the movement sufficient to cause a small tactile feedback signal to the user. Typically, the springs are sufficient for screen stability, but the addition of a detent additionally helps to prevent movement of the screen, even when touch-screens are used, as in some embodiments disclosed herein.

Figure 4:
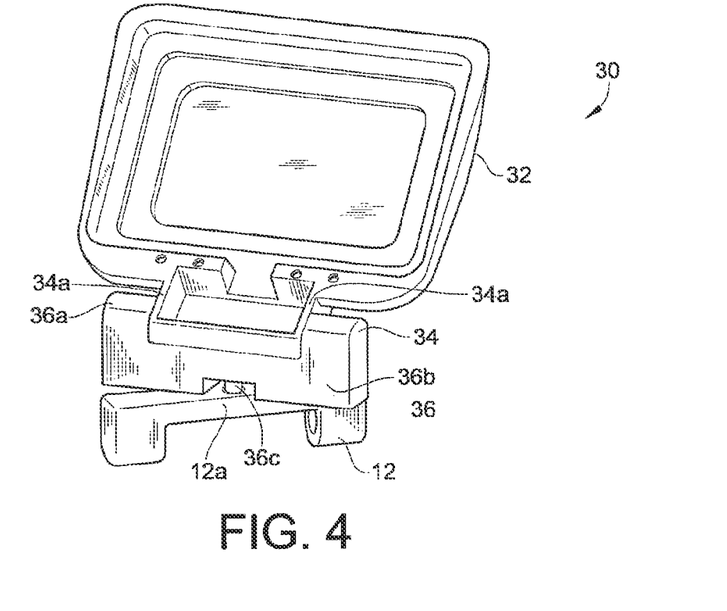
FIGS. 4-5 are alternate embodiments of hinges.
Figure 5:
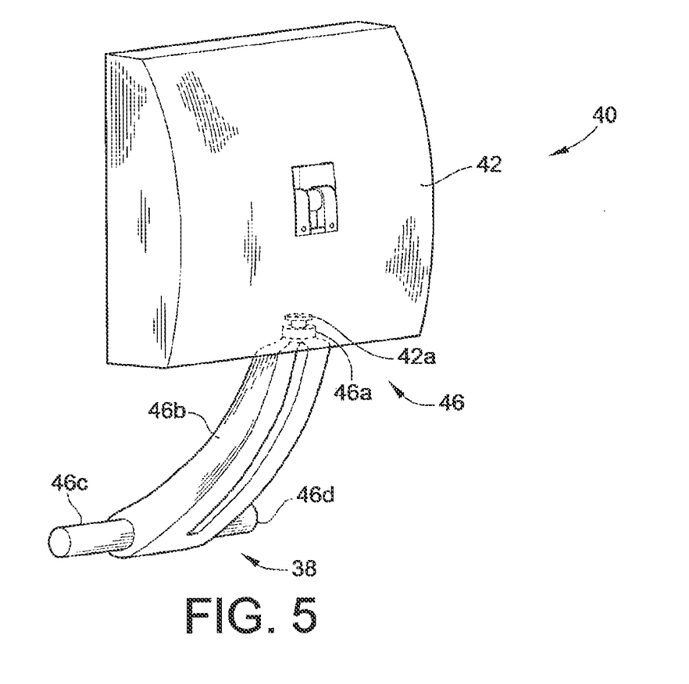

FIGS. 4-5 depict additional embodiments of hinges useful in the present disclosure. FIG. 4 depicts display portions of a dialysis machine 30. The display housing 32 is firmly attached to an upper swiveling hinge portion 34 in which the wires of the inductor or other device are embedded within webs 34a that connect the main part of the hinge to the display housing 32. The inductor within the upper hinge portion is not shown. Upper hinge portion 34 is tiltably and wirelessly connected to intermediate portion 36, which includes upper left and right hinge portions 36a, 36b. Hinge portions 36a, 36b each include an inductor for inductive coupling with the inductor within upper portion 34. In addition, the inductors within portions 36a, 36b are directly connected to an additional coil within intermediate portion 36 that fits within stem 36c. Collar 12a of dialysis machine 12 wirelessly accepts stem 36c, as described above for FIG. 2.

FIG. 5 depicts an additional embodiment, showing display portions of dialysis machine 40. Display screen 42 in this embodiment is rotatably and wirelessly attached via stem 42a to collar 46a of hinge 46. Hinge 46 with collar 46a, curved arm 46b allows rotation of display screen 42 with stem 42a about collar 46a. A second, swiveling hinge 38 is formed at the bottom end of arm 46b, which may be considered as an intermediate portion of both hinges. Left and right inductors 46c, 46d are formed within lower housing 46e and are directly connected to the inductor within collar 46a. The left and right inductors then fit tightly and swivelably within a matching portion of the dialysis machine housing.

Figure 6:
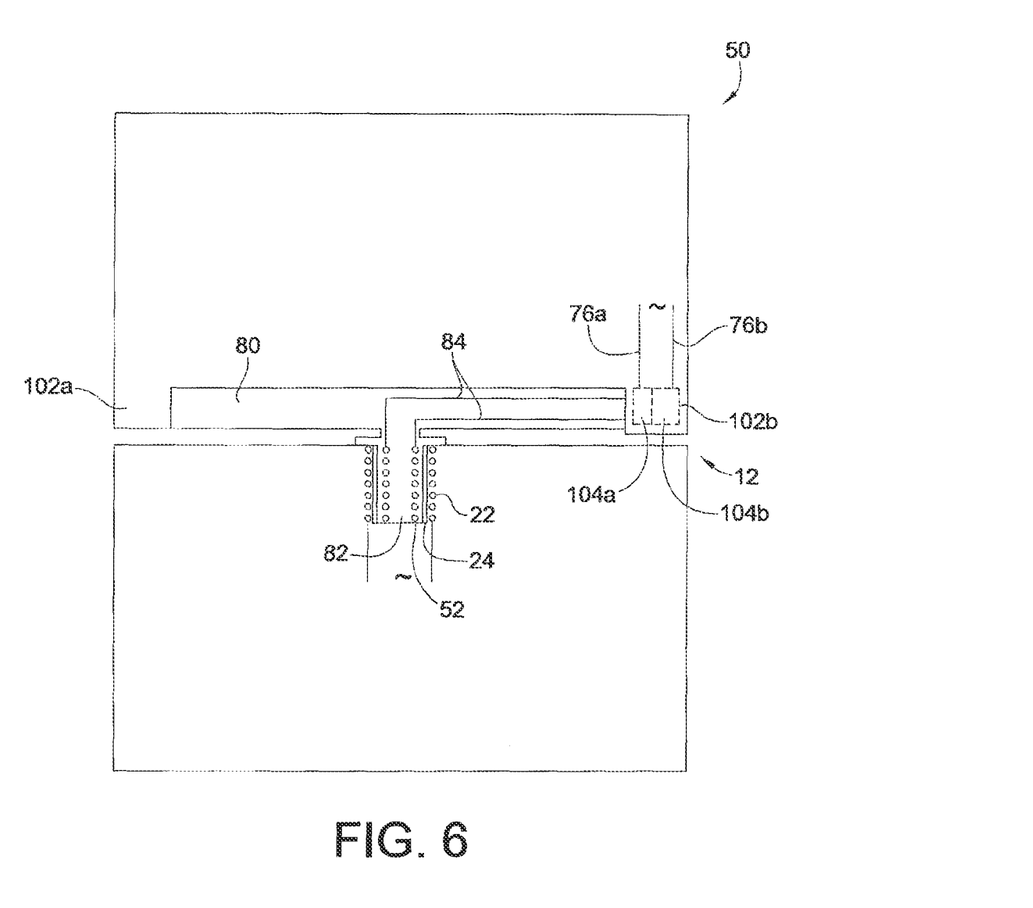
FIG. 6 is an elevation view of an additional embodiment.

Referring now to FIG. 6, a further alternative wireless coupling is illustrated. Here, the secondary coil 52 is located in stem 82 of hinge housing 80, similar to the embodiment of FIG. 2. Power regulation circuitry (not shown) conditions power for primary coil 22, which is located in base collar 24, here inset into instrument 12. Secondary coil 52 when induced with current sends the current traveling along wires or traces 84 to a pair of contacts (not illustrated), which are located on the outside of hinge housing 80. Hinge housing 80 is hinged inside hinges 102a and 102b of user interface 50. One of the hinges, e.g., hinge 102b, includes positive and negative contacts 104a and 104b located on the inside of hinge 102b, which mate with the outwardly exposed contacts of hinge housing 84 to transfer power via conductors 76a and 76b to power regulation circuitry (not shown) within user interface 50 for example. Although wires or traces 84 are shown going only to a single set of contacts, wires or traces 84 alternatively split to contacts located on both hinge sides 102a and 102b.

The tradeoff of the embodiment of FIG. 6 is the elimination of a second inductive coupling (FIG. 2) versus having exposed electrical contacts in the end of hinge housing 80 and inside one or both hinges 102a and 102b of user interface 50. User interface 50 of FIG. 6 is nevertheless coupled wirelessly to instrument 12 and moved readily in multiple dimensions.

Figure 7:
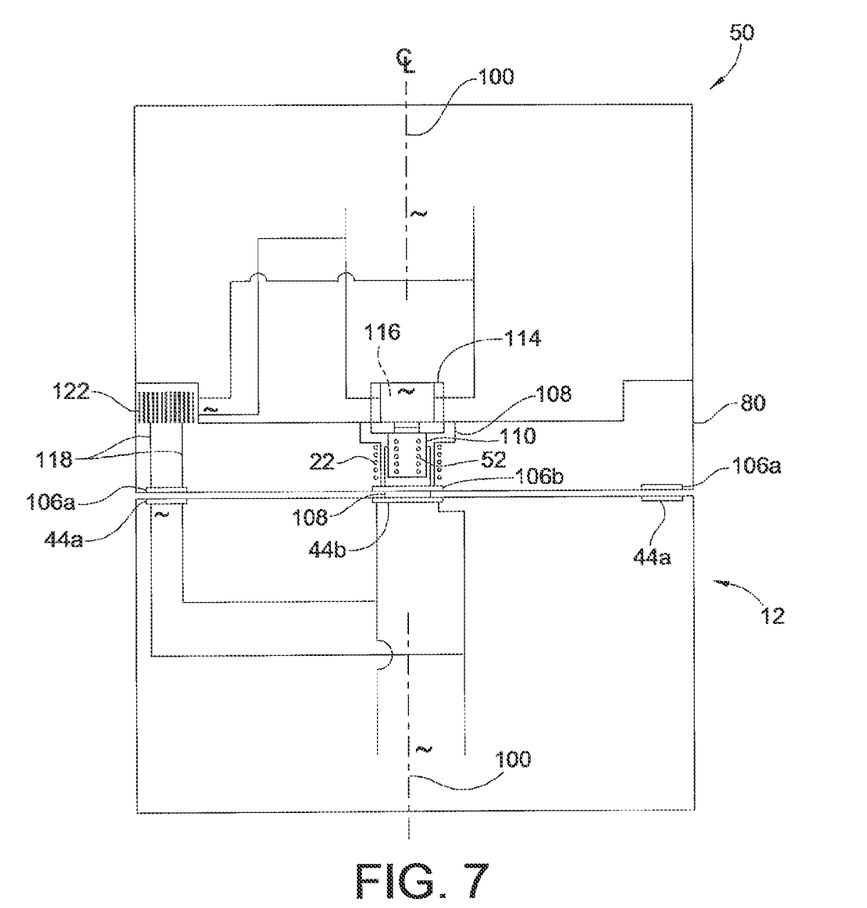
FIG. 7 is an elevation view of an alternative embodiment with a three-piece configuration.

A still further alternative inductive coupling is illustrated in FIG. 7. Here, line power or power from regulating circuitry powers two separate stationary contacts 44a and 44b. Contact ring 44a shown here in cross-section travels three hundred sixty degrees horizontally around the top of instrument 12. The same contact ring 44a is accordingly shown at the left and right sides of the instrument housing. Contact 44b is formed around collar 108 and resides at the approximate center of instrument 12. Both contacts 44a and 44b are stationary and do not rotate.

Hinge housing 80 rotates with respect to instrument 12, such that a first slip ring 106a of hinge housing 80 slides along the circular static contact ring 44a of instrument 12. A second, smaller, washer-shaped slip ring 106b of hinge housing 80 rotates about center-line 100 extending through hinge housing 80. Slip ring 106b is formed about a stem 110 provided in hinge housing 80. Slip ring 106b, in turn communicates with a primary coil 22 also wound about stem 110 of hinge housing 80.

Stem 110 resides within hinge housing 80. Stem 110 houses secondary coil 52. Current induced from primary coil 22 of housing 80 into secondary coil 52 of stem 110 is carried via conductors 112 to a contact 114, which can be u-shaped and formed to fit rotatably around a contact 116 of user interface 50, such that when user interface 50 is pivoted backwards and forwards, display contact 116 maintains an electrical connection with contact 114 of stem 110. Thus current delivered to contact 114 via conductors 112 and secondary coil 52 is in turn transferred to positive and negative leads of user interface 50 via the user interface contact 116.

Additionally, power delivered to contact ring 44a is transmitted to slip ring contact 106a which in turn is carried via conductors 118 to primary coil 122 located in a hinge portion 102a of hinge housing 80. Primary coil 122 induces a current into a second secondary coil (not illustrated) located within a hinge portion of user interface or display device 50, which is coupled rotatably to hinge portion 102a of hinge housing 80. Current induced into the second secondary coil (not illustrated) is again transferred to positive and negative leads within user interface 50 to, for example, power regulation circuitry 54 and components 56 to 70 as has been discussed herein.

The configuration of FIG. 7 provides a redundant wireless power supply from instrument 12 to user interface 50. The configuration of FIG. 7 also has exposed contacts, e.g., contacts 114 of stem 110 and inner contact 116 of user interface 50, but provides a wirelessly removable user interface that is positionable in multiple dimensions.

Inductive coupling as described above, is a very useful way of wirelessly transmitting information and power from a stationary machine treatment machine to a moveable screen. There are other ways and other embodiments that may also be used. Broadly, the embodiments envisioned include radio, microwave, and infrared transmission. Optical signals may also be used, but are not preferred because of the difficulty of long-term cleanliness of parts that are subject to spills of dialysate solution. In particular, hinges or other tilt or swivel mechanisms may be difficult to reach and to clean. In addition, physical limitations of the patients or users make frequent cleaning a challenging proposition. Additional embodiments are described in FIGS. 8-9

Figure 8:
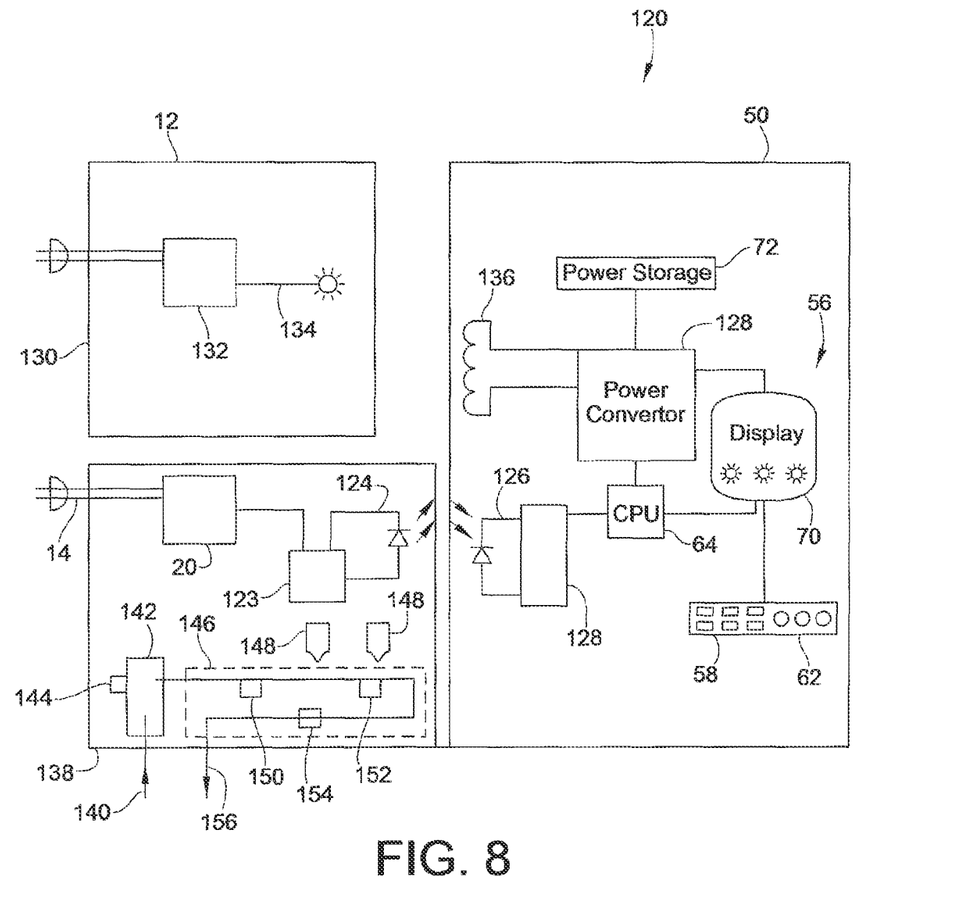
FIG. 8 depicts a wireless configuration using radio or microwave transmission, using "hot spot" wireless power transmission or recharging.
Figure 9:
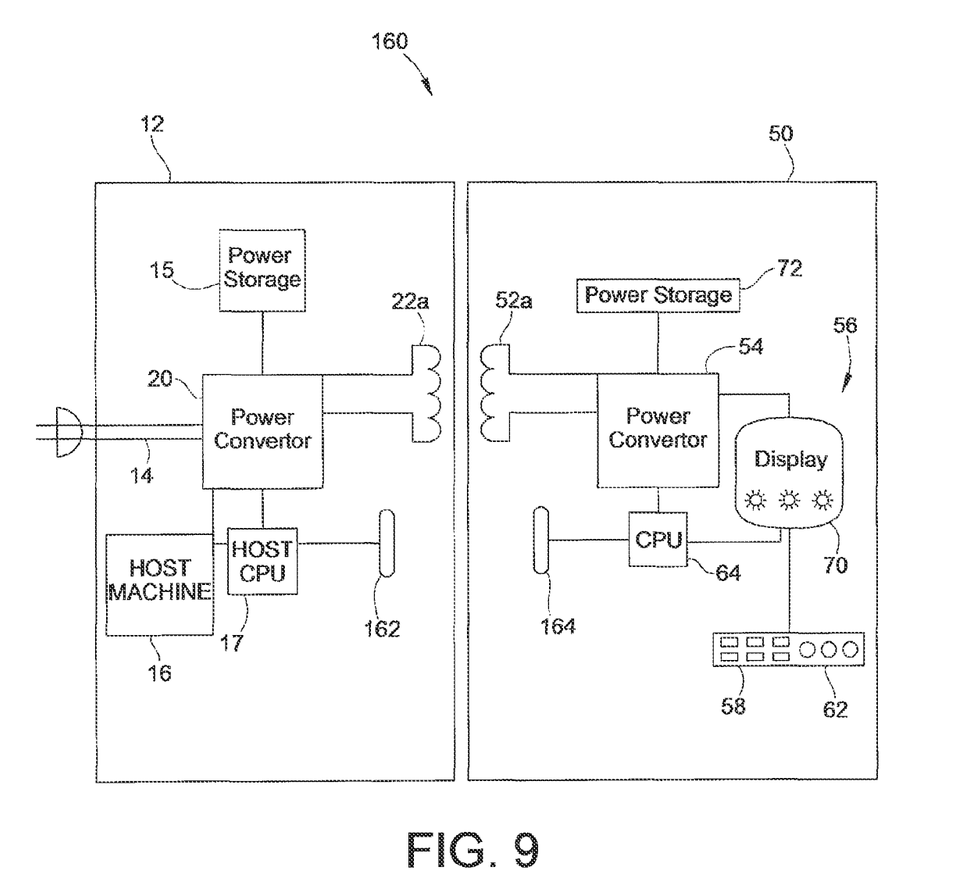
FIG. 9 depicts an additional wireless configuration using infrared transmission.

FIGS. 8-9 include many components in common with FIG. 1, which will not be repeated in this description. FIG. 8 depicts a dialysis machine with an optical link for operational control and a wireless power source. Dialysis machine 120 includes a base 138, a display 50 and a remote wireless power source 130, wherein remote means that the power source 130 is not within the dialysis machine. The base 138 includes a cord 14 for connecting to a power source, such as a convenience outlet. The base also includes a dialysis fluid input line 140 and a dialysis fluid output line 156, for connecting to a patient using the dialysis fluid. The base includes a heater 144 with a temperature sensor 142 and also includes a dialysis cassette 146. The dialysis cassette is inserted into the base 138. The cassette typically includes one or two pumps (not shown) and the base includes actuators 148 for operating the pumps. The cassette or the base may also include sensors for detecting and measuring the status and operation of the base, such as pressure sensors 150, 154 and fluid flow sensor 152. The sensors are operably connected to the host processor 123. In some embodiments, the pumps may be operated by motors, linear actuators or other prime movers, and there may be additional sensors that track operation or status of the pumps, such as encoders on the motors or position sensors on actuators. All of these are considered to be sensors.

In this embodiment, host processor 123 in the dialysis machine includes signal circuits and an optical link with optical emitter 124 for connecting with optical receiver 126 in display 50. The signal is decoded by processing circuitry 128 in the display 50. Techniques for encoding and decoding optical signals are well known, such as those using Texas Instruments, Plano, Tex., U.S.A. Digital signal processors (DSPs) within the signal processing circuitry 123, 128 may be used to both encode and decode the signals. Base 138 and display 50 may include both emitters and receivers for two-way communication.

The power link in this embodiment is also wireless, and may be provided by the dialysis machine itself or may be provided by another source, such as an external source or hot spot of inductive power. In this system, an external source 130 radiates electrical power, such as RF power, and it is received by inductor 136, acting as an antenna, within the display 50. The technique is similar to the techniques described for FIGS. 1-2, but with this technology, greater distances are possible than through normal inductive coupling at normal line power frequencies. Wireless power transmitter modules are available from companies such as Powercast Corp. (formerly FireFly Power Technologies, Inc.), Ligonier, Pa., and Fulton Innovation, LLC, Ada, Mich., U.S.A., which also owns Splashpower, Inc. (Cambridge, UK). Details of power conversion, transmission, and reception are included in many patents and applications of these companies. Examples include U.S. Pat. Appl. Publ. 2007/0298846, U.S. Pat. Appl. Publ. 2008/0169910, and U.S. Pat. No. 6,906,495, all of which are hereby incorporated by reference, as though each were fully set forth herein in full detail, and which are relied on In general, the system 130 for such wireless conversion include a radio transmitter 132, which converts electrical power (at 50 or 60 Hz) to radio frequency (RF), and an antenna 134, which may be an inductor. The receiver typically includes an antenna and processing circuitry, shown in FIG. 8 as an inductor 136 and power converter 128. The power is typically first converted to DC in the receiving module, and may then be rectified to a desired DC voltage or converted to the desired AC power level. If the power converter 128 includes a battery-charging circuit, the power may be stored in a battery or power storage unit 72.

Another embodiment of a wireless system is depicted in FIG. 9. In this embodiment, system 160 includes the power processing circuitry 20 and a host CPU 17. Electric power to operate display 50 is transmitted through the transformer formed by primary coils 22a, 52a, as described above. Signals and data are transmitted and received by the machine 12 using infrared radiation transmitter/receiver 162. The display 50 receives the signals using infrared transmitter/receiver 164, and the signals are then processed through display host computer 64. In some embodiments, the power processing may take place as shown, with separate inductors 22a, 52a. As noted above, however, other embodiments may have a separate power source via transmitted RF power. In other embodiments, the processing circuitry itself may act as a wireless RF power source, transmitting power wirelessly as does the source 130 in FIG. 8. This may take place during a time period before the dialyzing capability of the machine is used, or after the dialyzing portion of the machine is used, to charge power storage device 72.

Non-Hinged Embodiments

Technology in these areas has advanced to the point where it is not necessary to close-couple inductors using a hinge to transfer power. There are now magnetic and RF technologies that enable close-coupling that is suitable for remote power transmission between a dialysis machine cabinet or housing and a monitor or display device placed atop the cabinet within range suitable for magnetic or RF coupling of power from the dialysis machine to the display or monitor. Monitor or display embodiments using this technology typically have a flat base that stands proud from the monitor itself, the flat base suitable for enclosing a flat or planar coil, as described below, for receiving electric power, that is, electromagnetic energy. The dialysis machine may have a similar flat or planar coil near a top surface of the dialysis machine housing for emitting such energy in order to power the monitor or display.

Figure 10:
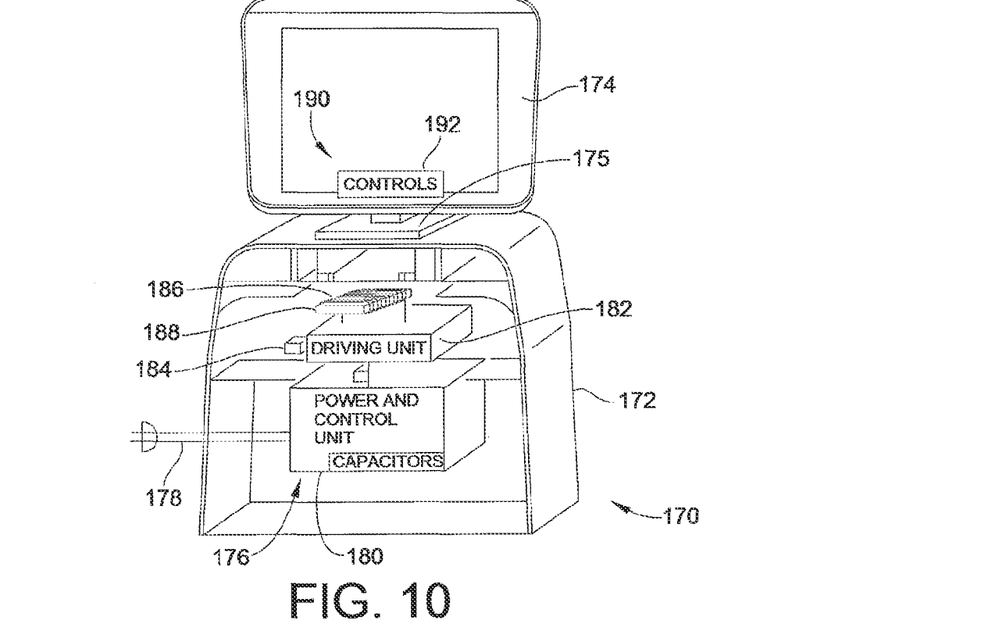
FIG. 10 depicts an additional wireless embodiment using magnetic transmission, in which the user interface sits upon a cabinet.

FIG. 10 depicts a dialysis machine 170 with a cabinet or housing 172 and a monitor or display 174, the display 174 having a base or foot 175 suitable for stable placement atop the cabinet. The base 175 is depicted as flat, but it may include downwardly-extending protrusions for placement into mating apertures in the top of the cabinet, in order to add additional stability for resisting movement of the monitor when the touch screen or other devices on the front face are engaged. In this embodiment, magnetic fields are used to transfer power wirelessly from a dialysis machine to a display.

The monitor 174 receives its power from an electromagnetic power source 176 within the dialysis machine housing 172. Such power sources are described in U.S. Pat. No. 6,906,495, assigned to Splashpower, Limited, Cambridge, U.K., which is hereby incorporated by reference in its entirety and is relied upon. Other useful information on this technology is found in U.S. Pat. Nos. 6,650,213; 7,042,196; and 7,239,110, all of which are hereby incorporated by reference in their entirety and relied upon. The power source 176 receives electricity from a convenience outlet via a typical power cord 178. Power source 176 includes a power and control unit 180, a driving unit 182 for generating current, and at least one magnetic coil 186 for transforming the current into electromagnetic energy. In one embodiment, the power source also includes magnetic material 188, to enhance and magnify the quantity of electromagnetic energy that may be produced by a given coil. The magnetic material functions in the present case much as an iron core functions for a transformer or inductor, to increase the saturation or capacity of the transformer or inductor. Examples of magnetic materials include mu-metal, Met-Glas™, Hiperco 50®, ferrite cores, steel or other materials with high saturation values and high magnetic permeability.

In this embodiment, the magnetic material and coil are desirably flat, so that the resulting magnetic field has a desirably flat shape that can be received in a close-coupled manner by the monitor 174. In one embodiment, the magnetic material is a thin, square or rectangular piece of magnetic material, with a flat coil wound thereupon. In this manner, the magnetic field and the electromagnetic energy form a relatively flat field, facilitating transfer of power to a nearby flat coil. Other embodiments may use an annular piece of magnetic material, e.g., a circular piece with a central aperture for winding a coil about the annular piece, or any other suitable shape. The coils may be described as flat or planar, as those seen in FIGS. 6G-6I, 6L and 7A of U.S. Pat. Nos. 7,042,196, 7,239,110, which are hereby incorporated by reference in their entirety and relied upon.

Monitor 174 includes a corresponding power conversion circuit 190, including controls 192, at least one coil and magnetic material. The coil and magnetic material function as a secondary winding for an inductor, receiving electromagnetic power wirelessly from power source 176. The magnetic power is then converted to usable energy by standard control circuitry 192, for use in the video monitor. The base 175 of the monitor 175 is placed atop or adjacent the coil 186 and magnetic material 188 of the power source 176. The dialysis machine cabinet 172 and the monitor 174 includes other circuitry as described for FIGS. 1-9 for two-way communication with the dialysis machine via radio or other wireless communication modes.

Figure 11:
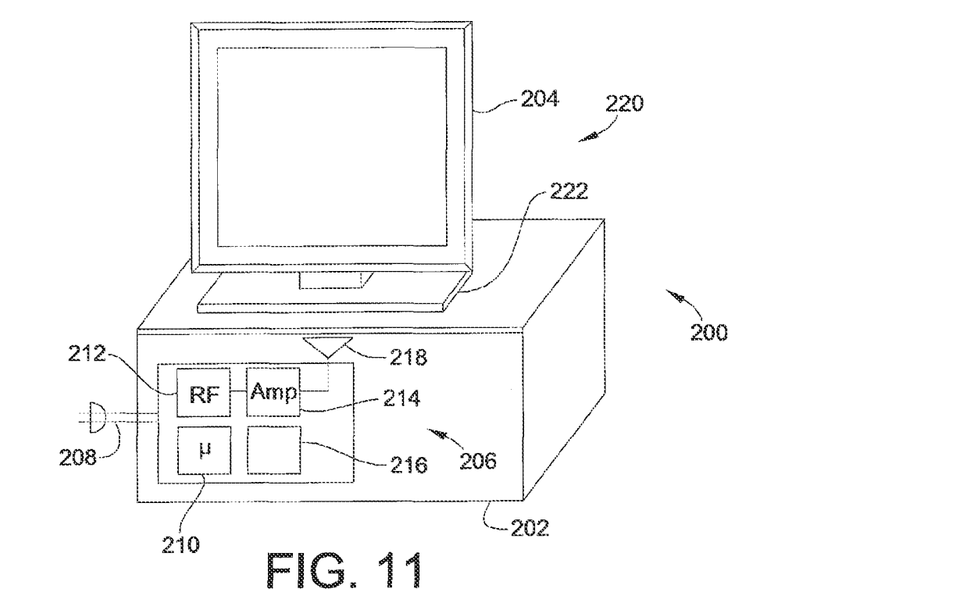
FIG. 11 depicts an additional wireless embodiment using a radio-frequency transmitter and receiver.

FIG. 11 depicts another embodiment using an RF power source within a dialysis cabinet to power a monitor or display atop the cabinet. A dialysis machine (not shown) includes a cabinet or housing 202 and a monitor or display 204, which may be a touch-screen monitor. The internals of the dialysis machine and the monitor are similar to those described above for FIGS. 1-9. In this embodiment, the dialysis machine includes an RF power source 206 to generate RF power, with corresponding circuitry (not shown) in the monitor 204 to received the RF power and convert it to useful AC and DC voltages. The monitor may also include, as noted in FIGS. 1 and 8-9, a power storage unit, such as a battery for storing the converted power. The control circuitry in these embodiments also includes a battery charging circuit, and as will be obvious, circuits for converting the RF power into the necessary AC and DC voltages to power the monitor and the additional circuitry.

The dialysis machine cabinet 202 and the power source 206 receive electricity through a power cord 208. The normal 50-60 Hz power is then converted into RF power by an RF generator 212 and may be amplified by appropriate amplifiers 214. The power is then radiated through an antenna 218, placed near the top surface of the cabinet to facilitate reception in the base 222 of the monitor 204. It will be recognized that the power source 206 includes other additional circuitry, such as a controller 210, power sensors 216, filters, couplers, and so forth, as described in U.S. Pat. No. 7,027,311, U.S. Pat. Appl. Publ. 2008/0169910, and U.S. Pat. Appl. Publ. 2006/0199620, which are assigned to Powercast Corp., Ligonier, Pa., U.S.A., and which are hereby incorporated by reference in their entirety and relied on. These documents describe wireless power transmission.

The RF energy is received within base 222 having a receiving antenna, one or more mating inductors, and an array of diodes and capacitors for converting the RF energy into a DC voltage. The DC voltage generated may then be rectified into the desired DC voltage or inverted into a desired AC voltage. These circuits are well-known to those with skill in the electrical arts, and are described, for example, in *Power Electronics: Converters, Applications and Design*, N. Mohan, T. M. Undeland, and W. P. Robbins, John Wiley & Sons, 1989, which is hereby incorporated by reference in its entirety and is relied on. See also FIG. 2 of U.S. Pat. No. 7,027,311.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A hinge for mechanically and electrically coupling a machine and a display wirelessly, comprising:
    a machine portion of the hinge having a first transceiver for wirelessly sending a signal concerning an operation or status of the machine; and
    a display portion of the hinge having a second transceiver for wirelessly receiving the operating signal,
    wherein the hinge machine portion and the hinge display portion are mechanically connected so as to: (i) swivel with respect to each other about a swivel axis, wherein at least one of the first transceiver or the second transceiver is spatially offset from the swivel axis; or (ii) tilt with respect to each other about a tilt axis, wherein at least one of the first transceiver or the second transceiver is spatially offset from the tilt axis.

2. The hinge of claim 1, wherein the first transceiver includes a first induction coil embedded within the hinge machine portion, and wherein the second transceiver includes a second induction coil embedded within the hinge display portion.

3. The hinge of claim 1, wherein at least one of the first and second transceivers includes at least one of an induction coil, an optical transducer, an optical LED, and an infrared transmitter.

4. The hinge of claim 1, wherein the hinge display portion is configured and arranged to (i) swivel and (ii) tilt with respect to the hinge machine portion.

5. The hinge of claim 1, further including an intermediate portion of the hinge mechanically connecting the hinge display portion to the hinge machine portion, the hinge intermediate portion configured and arranged to: (a) swivel with respect to one of the hinge machine portion or the hinge display portion; and (b) tilt with respect to the other of the hinge machine portion or the hinge display portion.

6. The hinge of claim 5, wherein the first transceiver includes a first induction coil embedded within the hinge machine portion, the second transceiver includes a second induction coil embedded within the hinge display portion, and further including third and fourth induction coils embedded within the hinge intermediate portion for transmitting the signal from the first induction coil to the second induction coil.

7. The hinge of claim 1, wherein the hinge machine portion includes a first electromagnetic coil for wirelessly transmitting electromagnetic power, and wherein the hinge display portion includes a second electromagnetic coil for wirelessly receiving the electromagnetic power.

8. A method of sending an electrical signal wirelessly through a hinge, comprising:
    mechanically connecting a display to a machine via a hinge that (i) enables the display to rotate with respect to the machine about a rotational axis and (ii) positions at least one transceiver to be spatially offset from the rotational axis;
    generating signals concerning an operation of the machine;
    using the at least one transceiver to wirelessly transmit at least one operating signal from the machine, through the hinge, to the display; and
    displaying information on the display based on the at least one operating signal.

9. The method of claim 8, further including swiveling or tilting the display via the hinge while at the same time wirelessly transmitting the at least one operating signal through the hinge.

10. The method of claim 8, wherein wirelessly transmitting the at least one operating signal includes inductively transmitting the at least one operating signal.

11. The method of claim 8, further including transmitting the at least one operating signal using radio waves, an optical signal or infrared energy.

12. The method of claim 8, further including generating electric power and wirelessly transmitting the electric power from the machine, through the hinge, and to the display to power a component of the display.

13. A method of sending an electrical signal wirelessly, comprising:
    providing a display configured and arranged to be removably and wirelessly connected to a machine;
    inductively transferring at least one operating signal for the machine from the display to the machine;
    supplying electric power to the machine;
    transferring electric power from the machine to the display when the display is mechanically connected to the machine;
    storing electric power within the display; and
    enabling the display to operate using the stored electric power when mechanically disconnected from the machine.

14. The method of claim 13, wherein transferring the at least one operating signal includes wirelessly transferring the at least one operating signal.

15. The method of claim 13, wherein transferring the electric power includes inductively sending the electric power.

16. The method of claim 13, which includes transferring the at least one operating signal and the electrical power through at least one mechanical connection between the machine and the display.

17. The method of claim 13, which includes transferring the electric power at a frequency between about 20 kHz and about 1 MHz.

18. The method of claim 13, which includes inductively transferring the electric power and transferring the at least one operating signal via radio waves, optical signals or infrared energy.

19. A method of sending an electrical signal wirelessly, comprising:
    providing a display configured and arranged to be removably and wirelessly connected to a medical machine;
    inductively transferring at least one operating signal for the medical machine between the medical machine and the display;
    supplying electric power to the medical machine;
    transferring electric power from the medical machine to the display when the display is mechanically connected to the medical machine;
    storing electric power within the display; and enabling the display to operate using the stored electric power when mechanically disconnected from the machine.

* * * * *